US005624704A

United States Patent [19]
Darouiche et al.

[11] Patent Number: 5,624,704
[45] Date of Patent: Apr. 29, 1997

[54] ANTIMICROBIAL IMPREGNATED CATHETERS AND OTHER MEDICAL IMPLANTS AND METHOD FOR IMPREGNATING CATHETERS AND OTHER MEDICAL IMPLANTS WITH AN ANTIMICROBIAL AGENT

[75] Inventors: Rabih O. Darouiche; Issam Raad, both of Houston, Tex.

[73] Assignees: Baylor College of Medicine, Houston; University of Texas System, Austin, both of Tex.

[21] Appl. No.: 427,379

[22] Filed: Apr. 24, 1995

[51] Int. Cl.$^6$ .............................. B05D 3/12; B05D 10/34; B05D 7/02
[52] U.S. Cl. .................. 427/2.24; 427/2.3; 427/2.28; 427/353; 427/369; 427/430.1
[58] Field of Search .................. 427/2.3, 2.25, 427/2.24, 352, 369, 393.5, 430.1, 2.28, 353; 604/265

[56] References Cited

U.S. PATENT DOCUMENTS

| | | | |
|---|---|---|---|
| 3,695,921 | 10/1972 | Shepherd et al. | 427/2.3 |
| 4,581,028 | 4/1986 | Fox et al. | 623/2 |
| 4,592,920 | 6/1986 | Murtfeldt | 427/2.3 |
| 4,603,152 | 7/1986 | Laurin et al. | 604/265 |
| 4,605,564 | 8/1986 | Kulla et al. | 604/265 |
| 4,612,337 | 9/1986 | Fox et al. | 523/113 |
| 4,642,104 | 2/1987 | Sakamoto et al. | 604/264 |
| 4,723,950 | 2/1988 | Lee | 604/322 |
| 4,842,575 | 6/1989 | Hoffman, Jr. et al. | 427/2.25 |
| 4,895,566 | 1/1990 | Lee | 604/266 |
| 4,917,686 | 4/1990 | Bayston et al. | 604/265 |
| 4,925,668 | 5/1990 | Khan et al. | 424/422 |
| 4,999,210 | 3/1991 | Solomon et al. | |
| 5,013,306 | 5/1991 | Solomon et al. | |
| 5,019,096 | 5/1991 | Fox et al. | 623/1 |
| 5,165,952 | 11/1992 | Solomon et al. | 427/2 |
| 5,217,493 | 6/1993 | Raad et al. | 623/11 |
| 5,344,411 | 9/1994 | Domb et al. | 623/11 |
| 5,362,754 | 11/1994 | Raad et al. | 514/566 |
| 5,484,565 | 1/1996 | Larsen et al. | 427/2.3 |
| 5,494,765 | 2/1996 | Siegel | 427/2.11 |
| 5,516,480 | 5/1996 | Krall et al. | 427/2.24 |

OTHER PUBLICATIONS

Kamal, Gagan D., *Reduced Intravascular Catheter Infection by Antibiotic Bonding*, JAMA, May 8, 1991, vol. 265, No. 18, pp. 2364–2368.

Raad, Issam I., et al., *Infectious Complications of Indwelling Vascular Catheters*, Clinical Infectious Diseases, 1992, pp. 197–208 (no month).

Goëau–Brissonnière, Olivier, et al., *Prevention of Vascular Graft Infection by Rifampin Bonding to a Gelatin–Sealed Dacron Graft*, Ann. Vasc. Surg. 1991,pp. 408–412 (no month).

Sheretz, Robert J., et al., *Efficacy of Antibiotic–Coated Catheters in Preventing Subcutaneous Staphylococcus aureus Infection in Rabbits*, The Journal of Infectious Diseases, 1993, pp. 98–106 Jan.

Maki, D.G., et al., *Clinical Trial of a Novel Antiseptic Central Cenous Catheter*, Abstracts of the 1991 ICAAC, p. 176 (no month).

*Primary Examiner*—Diana Dudash
*Attorney, Agent, or Firm*—Fulbright & Jaworski L.L.P.

[57] ABSTRACT

A non-metallic antimicrobial impregnated medical implant, such as a catheter, and a method for impregnating a non-metallic medical implant with an antimicrobial agent is provided. The method for making the impregnated implant comprises the steps of forming an antimicrobial composition of an effective concentration to inhibit the growth of organisms, such as staphylococci, other gram-positive bacteria, gram-negative bacilli and Candida and applying the antimicrobial composition to at least a portion of the medical implant under conditions where the antimicrobial composition permeates the material of the medical implant. The antimicrobial composition is formed by dissolving an antimicrobial agent in an organic solvent, adding a penetrating agent to the composition, and adding an alkalinizing agent to the composition. The antimicrobial composition is preferably heated to a temperature between about 30° C. and 70° C. prior to applying the composition to the medical implant to enhance the adherence of the antimicrobial agent to the medical implant material. After the impregnated implant is removed from the antimicrobial solution, the impregnated implant is allowed to dry then rinsed with a liquid and milked to remove excess granular deposits and ensure uniform color of the impregnated implant.

33 Claims, No Drawings

ANTIMICROBIAL IMPREGNATED CATHETERS AND OTHER MEDICAL IMPLANTS AND METHOD FOR IMPREGNATING CATHETERS AND OTHER MEDICAL IMPLANTS WITH AN ANTIMICROBIAL AGENT

BACKGROUND OF THE INVENTION

1. Field of the Invention

The present invention relates to indwelling medical devices, such as catheters, the material of which is impregnated with one or more antimicrobial agents to inhibit the growth of bacterial and fungal organisms, such as staphylococci, other gram-positive bacteria, gram-negative bacilli and Candida. The invention also relates to a method of impregnating the indwelling medical device with one or more antimicrobial agents, such as minocycline and rifampin.

2. Description of the Prior Art

Indwelling medical devices including vascular catheters are becoming essential in the management of hospitalized patients by providing venous access. The benefit derived from these catheters as well as other types of medical devices such as peritoneal catheters, cardiovascular devices, orthopedic implants and other prosthetic devices is often offset by infectious complications. The most common organisms causing these infectious complications are *Staphylococcus epidermidis* and *Staphylococcus aureus*. In the case of vascular catheters, these two organisms account for almost 70–80% of all infectious organisms, with *Staphylococcus epidermidis* being the most common organism. *Candida albicans*, a fungal agent, accounts for about 10–15% of catheter infections.

Another common hospital-acquired infection is urinary tract infection (UTI). The majority of cases of UTI are associated with the use of urinary catheters, including transurethral foley, suprapubic and nephrostomy catheters. These urinary catheters are inserted in a variety of populations, including the elderly, stroke victims, spinal cord-injured patients, post-operative patients and those with obstructive uropathy. Despite adherence to sterile guidelines for the insertion and maintenance of urinary catheters, catheter-associated UTI continues to pose a major problem. For instance, it is estimated that almost one-quarter of hospitalized spinal cord-injured patients develop symptomatic UTI during their hospital course. Gram-negative bacilli account for almost 60–70%, enterococci for about 25% and Candida species for about 10% of cases of UTI.

Colonization of bacteria on the surfaces of the catheter or other part of the device can produce serious patient problems, including the need to remove and/or replace the implanted device and to vigorously treat secondary infective conditions. A considerable amount of attention and study has been directed toward preventing such colonization by the use of antimicrobial agents, such as antibiotics, bound to the surface of the materials employed in such devices. In such attempts the objective has been to produce a sufficient bacteriostatic or bactericidal action to prevent colonization.

Various methods have previously been employed to coat the surfaces of medical devices with an antibiotic. For example, one of the simplest methods would be to flush the surfaces of the device with a solution of the antibiotic combination. Generally, coating the surfaces by a simple flushing technique would require convenient access to the implantable device. For example, catheters are generally amenable to flushing with a solution of rifampin and minocycline or rifampin and novobiocin. For use in flushing solutions, the effective concentration of the antibiotic would range from about 1 to 10 µg/ml for minocycline, preferably about 2 µg/ml; 1 to 10 µg/ml for rifampin, preferably about 2 µg/ml; and 1 to 10 µg/ml for novobiocin, preferably about 2 µg/ml. The flushing solution would normally be composed of sterile water or sterile normal saline solutions.

Another known method of coating the devices would be to first apply or absorb to the surface of the medical device a layer of tridodecylmethyl ammonium chloride (TDMAC) surfactant followed by an antibiotic coating layer. For example, a medical device having a polymeric surface, such as polyethylene, silastic elastomers, polytetrafluoroethylene or Dacron, can be soaked in a 5% by weight solution of TDMAC for 30 minutes at room temperature, air dried, and rinsed in water to remove excess TDMAC. Alternatively, TDMAC precoated catheters are commercially available. For example, central vascular catheters coated with TDMAC are available from Cook Critical Care, Bloomington, Ind. The device carrying the absorbed TDMAC surfactant coating can then be incubated in an antibiotic solution for up to one hour or so, allowed to dry, then washed in sterile water to remove unbound antibiotic and stored in a sterile package until ready for implantation. In general, the antibiotic solution is composed of a concentration of 0.01 mg/ml to 60 mg/ml of each antibiotic in an aqueous pH 7.4–7.6 buffered solution, sterile water, or methanol. According to one method, an antibiotic solution of 60 mg of minocycline and 30 mg of rifampin per ml of solution is applied to the TDMAC coated catheter.

A further method known to coat the surface of medical devices with antibiotics involves first coating the selected surfaces with benzalkonium chloride followed by ionic bonding of the antibiotic composition. See, e.g., Solomon, D. D. and Sherertz, R. J., J. Controlled Release, 6:343–352 (1987) and U.S. Pat. No. 4,442,133.

Other methods of coating surfaces of medical devices with antibiotics are taught in U.S. Pat. No. 4,895,566 (a medical device substrate carrying a negatively charged group having a pKa of less than 6 and a cationic antibiotic bound to the negatively charged group); U.S. Pat. No. 4,917,686 (antibiotics are dissolved in a swelling agent which is absorbed into the matrix of the surface material of the medical device); U.S. Pat. No. 4,107,121 (constructing the medical device with ionogenic hydrogels, which thereafter absorb or ionically bind antibiotics); U.S. Pat. No. 5,013,306 (laminating an antibiotic to a polymeric surface layer of a medical device); and U.S. Pat. No. 4,952,419 (applying a film of silicone oil to the surface of an implant and then contacting the silicone film bearing surface with antibiotic powders).

These and many other methods of coating medical devices with antibiotics appear in numerous patents and medical journal articles. Practice of the prior art coating methods results in a catheter or medical device wherein only the surface of the device is coated with the antibiotic. While the surface coated catheter does provide effective protection against bacteria initially, the effectiveness of the coating diminishes over time. During use of the medical device or catheter, the antibiotics leach from the surface of the device into the surrounding environment. Over a period of time, the amount of antibiotics present on the surface decreases to a point where the protection against bacteria is no longer effective.

Accordingly, there is a need for a catheter or medical device that can remain in vivo for extended periods of time without losing its antimicrobial efficacy. There is also a need for an easy and inexpensive method of applying an antimicrobial agent to a medical device, such as a catheter, that provides protection against bacterial and fungal organisms for extended periods of time.

SUMMARY OF THE INVENTION

An object of the present invention is to provide a medical implant and a method for coating a medical implant wherein an antimicrobial agent penetrates the exposed surfaces of the implant and is impregnated throughout the material of the implant.

A further object of the invention is to provide a practical, inexpensive, safe and effective method for coating or impregnating the material of various types of catheters and other medical implants with antimicrobial agents, such as rifampin and minocycline.

Still another object of the invention is to apply an antimicrobial agent to a catheter or other medical implant that provides a rather prolonged protection against a variety of bacterial and fungal organisms.

Thus in accomplishing the foregoing objects, there is provided in accordance with one aspect of the present invention a method for impregnating a non-metallic medical implant with an antimicrobial agent comprising the steps of forming an antimicrobial composition of an effective concentration to inhibit the growth of bacterial and fungal organisms by dissolving the antimicrobial agent in an organic solvent and adding a penetrating agent to the composition; and applying the antimicrobial composition to at least a portion of medical implant under conditions where the antimicrobial composition permeates the material of the medical implant.

In the preferred embodiment, the step of forming an antimicrobial composition may also include the step of adding an alkalinizing agent to the composition in order to enhance the reactivity of the material of the medical implant. Further according to the preferred embodiment, the antimicrobial composition is heated to a temperature between about 30° C. and 70° C. prior to applying the composition to the medical implant. The increased temperature enhances the adherence of the antimicrobial agent to the medical implant material. After the impregnated implant is removed from the antimicrobial solution and allowed to dry, the impregnated implant is preferably rinsed with a liquid and milked to remove excess granular deposits and ensure uniform color of the impregnated implant. The antimicrobial composition may be applied to the medical implant by dipping the implant into the antimicrobial composition for a period of between 15 and 120 minutes, and then removing the impregnated implant from the composition. Preferably, the implant is dipped in the composition for a period of approximately 60 minutes.

A further aspect of the present invention is an implantable medical device comprising a medical implant comprising a non-metallic material, and an antimicrobial composition, of an effective concentration to inhibit the growth of bacterial and fungal organisms, coating the surface of the implant and impregnating the non-metallic material of the medical implant. According to the preferred embodiment, the antimicrobial composition comprises a mixture of an antimicrobial agent, an organic solvent and a penetrating agent. The antimicrobial composition may further comprise an alkalinizing agent.

The non-metallic material of the medical implant is preferably selected from the group consisting of rubber, plastic, silicone, polyurethane, polyethylene, polytetrafluoroethylene, polyethylene tetraphthalate and polyethylene tetraphthalate sealed with gelatin, collagen or albumin.

Antibiotics such as tetracyclines (i.e. minocycline), penicillins, (i.e. nafcillin), macrolides (i.e. erythromycin), rifampin and combinations thereof may be used as an antimicrobial agent. Antiseptics, (i.e. hexachlorophene), disinfectants and synthetic moieties may also be used. Preferably, the antimicrobial agent comprises a combination of minocycline and rifampin.

The organic solvent may be selected from the group consisting of alcohols (i.e. methanol, ethanol), ketones (i.e. acetone, methylethylketone), ethers (i.e. tetrahydrofuran), aldehydes (i.e. formaldehyde), acetonitrile, acetic acid, methylene chloride and chloroform.

The penetrating agent is an organic compound selected from the group consisting of esters (i.e. ethyl acetate, propyl acetate, butyl acetate, amyl acetate, and combinations thereof), ketones (i.e. acetone, methylethylketone), methylene chloride and chloroform.

A variety of alkalinizing agents, both organic and inorganic, can be used, including sodium hydroxide, potassium hydroxide, ammonia in water (27% ammonium hydroxide), diethylamine and triethylamine. Due to their high ionic strength, salts such as sodium chloride, potassium chloride and ammonium acetate, may be used as a substitute for the alkalinizing agent to enhance the receptivity of the medical implant material.

The medical implant may be selected from a variety of vascular catheters such as peripherally insertable central venous catheters, dialysis catheters, long term tunneled central venous catheters, peripheral venous catheters, single-lumen and multiple-lumen short-term central venous catheters, arterial catheters and pulmonary artery Swan-Ganz catheters. Alternatively, the medical implant may be selected from a variety of other medical implants such as urinary catheters, other long term urinary devices, tissue bonding urinary devices, penile prostheses, vascular grafts, vascular catheter ports, wound drain tubes, hydrocephalus shunts, peritoneal dialysis catheters pacemaker capsules, artificial urinary sphincters, small or temporary joint replacements, urinary dilators and heart valves.

Other and further objects, features and advantages will be apparent and eventually more readily understood from a reading of the following specification, wherein examples of the presently preferred embodiments of the invention are given for the purpose of disclosure.

DESCRIPTION OF THE PREFERRED EMBODIMENT

The term "antimicrobial agent" as used in the present invention means antibiotics, antiseptics, disinfectants and synthetic moieties, and combinations thereof, that are soluble in organic solvents such as alcohols, ketones, ethers, aldehydes, acetonitrile, acetic acid, methylene chloride and chloroform.

Classes of antibiotics that can possibly be used include tetracyclines (i.e. minocycline), rifamycins (i.e. rifampin), macrolides (i.e. erythromycin), penicillins (i.e. nafcillin), cephalosporins (i.e. cefazolin), other beta-lactam antibiotics (i.e. imipenem, aztreonam), aminoglycosides (i.e. gentamicin), chloramphenicol, sufonamides (i.e. sulfamethoxazole), glycopeptides (i.e. vancomycin), quinolones (i.e. ciprofloxacin), fusidic acid, trimethoprim, metronidazole, clindamycin, mupirocin, polyenes (i.e.

amphotericin B), azoles (i.e. fluconazole) and beta-lactam inhibitors (i.e. sulbactam).

Examples of specific antibiotics that can be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. Other examples of antibiotics, such as those listed in Sakamoto et al., U.S. Pat. No. 4,642,104, herein incorporated by reference, will readily suggest themselves to those of ordinary skill in the art.

Examples of antiseptics and disinfectants are hexachlorophene, cationic bisiguanides (i.e. chlorhexidine, cyclohexidine) iodine and iodophores (i.e. povidone-iodine), para-chloro-meta-xylenol, triclosan, furan medical preparations (i.e. nitrofurantoin, nitrofurazone), methenamine, aldehydes (glutaraldehyde, formaldehyde) and alcohols. Other examples of antiseptics and disinfectants will readily suggest themselves to those of ordinary skill in the art.

Minocycline is a semisynthetic antibiotic derived from tetracycline. It is primarily bacteriostatic and exerts its antimicrobial effect by inhibiting protein synthesis. Minocycline is commercially available as the hydrochloride salt which occurs as a yellow, crystalline powder and is soluble in water and slightly soluble in organic solvents including alcohols, ketones, ethers, aldehydes, acetonitrile, acetic acid, methylene chloride and chloroform. Minocycline is active against a wide range of gram-positive and gram-negative organisms.

Rifampin is a semisynthetic derivative of rifamycin B, a macrocyclic antibiotic compound produced by the mold *Streptomyces mediterranic*. Rifampin inhibits bacterial DNA-dependent RNA polymerase activity and is bactericidal in nature. Rifampin is commercially available as a red-brown crystalline powder and is very slightly soluble in water and freely soluble in acidic aqueous solutions and organic solutions including alcohols, ketones, ethers, aldehydes, acetonitrile, acetic acid, methylene chloride and chloroform. Rifampin possesses a broad spectrum activity against a wide range of gram-positive and gram-negative bacteria.

Erythromycin is a macrolide antibiotic produced by a strain of *Streptomyces erythreaus*. Erythromycin exerts its antibacterial action by inhibition of protein synthesis without affecting nucleic acid synthesis. It is commercially available as a white to off-white crystal or powder slightly soluble in water and soluble in organic solutions including alcohols, ketones, ethers, aldehydes, acetonitrile, acetic acid, methylene chloride and chloroform. Erythromycin is active against a variety of gram-positive and gram-negative bacteria.

Nafcillin is a semisynthetic penicillin that is effective against both penicillin-G-sensitive and penicillin-G-resistant strains of *Staphylococcus aureus* as well as against pneumococcus, beta-hemolytic streptococcus, and alpha streptococcus (viridans streptococci). Nafcillin is readily soluble in both water and organic solutions including alcohols, ketones, ethers, aldehydes, acetonitrile, acetic acid, methylene chloride and chloroform.

Hexachlorophene is a bacteriostatic antiseptic cleansing agent that is active against staphylococci and other gram-positive bacteria. Hexachlorophene is soluble in both water and organic solutions including alcohols, ketones, ethers, aldehydes, acetonitrile, acetic acid, methylene chloride and chloroform.

These antimicrobial agents can be used alone or in combination of two or more of them. The antimicrobial agents are dispersed throughout the material of the medical device. The amount of each antimicrobial agent used to impregnate the medical device varies to some extent, but is at least of an effective concentration to inhibit the growth of bacterial and fungal organisms, such as staphylococci, gram-positive bacteria, gram-negative bacilli and Candida.

The term "organic solvent" as used in the present invention means solvents that can be used to dissolve antimicrobial agents, including alcohols (i.e. methanol, ethanol), ketones (acetone, methylethylketone), ethers (tetrahydrofuran), aldehydes (formaldehyde), acetonitrile, acetic acid, methylene chloride and chloroform.

The term "penetrating agent" as used in the present invention means an organic compound that can be used to promote penetration of the antimicrobial agent into the material of the medical device. Examples of these organic compounds are esters (i.e. ethyl acetate, propyl acetate, butyl acetate, amyl acetate, and combinations thereof), ketones (i.e. acetone and methylethylketone), methylene chloride and chloroform.

The term "alkalinizing agent" as used in the present invention means organic and inorganic bases including sodium hydroxide, potassium hydroxide, ammonia in water (27% ammonium hydroxide), diethylamine and triethylamine.

The term "high ionic strength salts" as used in the present invention means salts exhibiting high ionic strength, such as sodium chloride, potassium chloride and ammonium acetate. These salts may act both as an alkalinizing agent and as a penetrating agent to enhance the receptivity of the medical implant material.

The term "bacterial and fungal organisms" as used in the present invention means all genuses and species of bacteria and fungi, including but not limited to all spherical, rod-shaped and spiral bacteria. Some examples of bacteria are stapylococci (i.e. *Staphylococcus epidermidis, Staphylococcus aureus*), *Enterrococcus faecalis, Pseudomonas aeruginosa, Escherichia coli*, other gram-positive bacteria and gram-negative bacilli. One example of a fungus is *Candida albicans*.

The medical devices that are amenable to impregnation by the antimicrobial combinations are generally comprised of a non-metallic material such as thermoplastic or polymeric materials. Examples of such materials are rubber, plastic, polyethylene, polyurethane, silicone, Gortex (polytetrafluoroethylene), Dacron (polyethylene tetraphthalate), Teflon (polytetrafluoroethylene), latex, elastomers and Dacron sealed with gelatin, collagen or albumin.

Particular devices especially suited for application of the antimicrobial combinations of this invention include peripherally insertable central venous catheters, dialysis catheters, long term tunneled central venous catheters, peripheral venous catheters, short-term central venous catheters, arterial catheters, pulmonary artery Swan-Ganz catheters, urinary catheters, long term urinary devices, tissue bonding urinary devices, penile prostheses, vascular grafts, vascular catheter ports, wound drain tubes, hydrocephalus shunts, peritoneal catheters, pacemaker capsules, artificial urinary sphincters, small or temporary joint replacements, urinary dilators, heart valves and the like.

One embodiment of the present invention is a method for impregnating a non-metallic medical implant with an antimicrobial agent comprising the steps of forming an antimicrobial composition of an effective concentration to inhibit the growth of bacterial and fungal organisms by dissolving the antimicrobial agent in an organic solvent and adding a penetrating agent to the composition; and applying the antimicrobial composition to at least a portion of medical implant under conditions where the antimicrobial composition permeates the material of the medical implant.

In a preferred embodiment, the step of forming an antimicrobial composition may also include the step of adding an alkalinizing agent to the composition in order to enhance the reactivity of the material of the medical implant. Further according to the preferred embodiment, the antimicrobial composition is heated to a temperature between about 30° C. and 70° C. prior to applying the composition to the medical implant to increase the adherence of the antimicrobial agent to the medical implant material. After the impregnated implant is removed from the antimicrobial solution and allowed to dry, the impregnated implant is preferably rinsed with a liquid and milked to remove excess granular deposits and ensure uniform color of the impregnated implant. The antimicrobial composition may be applied to the medical implant by dipping the implant into the antimicrobial composition for a period of between 15 and 120 minutes, and then removing the impregnated implant from the composition. Preferably, the implant is dipped in the composition for a period of approximately 60 minutes.

The method of the present invention preferably comprises a single step of applying an antimicrobial composition to the surfaces of a medical implant. However, it is expected that several applications of the antimicrobial agent, or other substances, can be applied to the surfaces of the implant without affecting the adherence of the antimicrobial agent to the implant.

A preferred embodiment of the method for impregnating a catheter with an antimicrobial agent comprises the steps of (1) forming an antimicrobial composition of an effective concentration to inhibit the growth of bacterial and fungal organisms, such as staphylococci, other gram-positive bacteria, gram-negative bacilli and Candida, by (a) dissolving an antimicrobial agent in an organic solvent, (b) adding a penetrating agent to the antimicrobial agent and organic solvent composition, (c) adding an alkalinizing agent to the composition to improve the reactivity of the material of the medical implant; (2) heating the antimicrobial composition to a temperature of between about 30° C. and 70° C. to enhance the adherence of the antimicrobial agent to the material of the medical device; (3) applying the antimicrobial composition to the medical implant, preferably by dipping the implant in the composition for a period of about 60 minutes and under conditions where the antimicrobial composition permeates the material of the medical device; (4) removing the impregnated medical implant from the antimicrobial composition and allowing it to dry; and (5) rinsing the impregnated medical implant with a liquid and milking the impregnated medical implant.

A further embodiment of the present invention is an implantable medical device comprising a medical implant comprising a non-metallic material, and an antimicrobial composition, of an effective concentration to inhibit the growth of bacterial and fungal organisms, coating the surface of the implant and impregnating the non-metallic material of the medical implant.

According to a preferred embodiment, the antimicrobial composition comprises a mixture of an antimicrobial agent, an organic solvent and a penetrating agent. The antimicrobial composition may further comprise an alkalinizing agent. The preferred antimicrobial agent for use in the antimicrobial composition is a combination of minocycline and rifampin.

The following examples are offered by way of illustration and are not intended to limit the invention in any manner.

EXAMPLE 1

Basic Antimicrobial Impregnation Method 450 mg of NaOH were dissolved in 45 ml of methanol while stirring until clear, yielding a concentration of 10 mg NaOH per ml of methanol. The dissolution was more rapidly achieved while stirring on a hot plate at a temperature of about 45° C. The final pH was about 12.1, taking into consideration that the pH in organic solvents may not be very reproducible.

4.5 g of minocycline were added in small aliquots over 1 hour to the above solution while stirring at a temperature of about 45° C. until clear. Then 9 g of rifampin were added in small aliquots over 15 minutes while stirring at a temperature of about 45° C. until clear.

255 ml of butyl acetate (pre warmed to 45° C.) were added in aliquots to the above solution while continuously stirring at 45° C. to keep the solution clear (antibiotics dissolve much more in methanol than in butyl acetate).

Catheters (whole silicone catheters, polyurethane shafts and polyethylene shafts) were dipped in the antimicrobial solution, which contains 15 mg of minocycline and 30 mg of rifampin per ml of the 15:85 mixture of methanol:butyl acetate, for 1 hour at 45° C.

Catheters were removed from the antimicrobial solution and allowed to dry for at least 8 hours (preferably overnight). Catheters were then rinsed and gently milked under the water faucet to ensure uniform color, then allowed to dry for at least 2 hours before testing. It was noted that the uniform color of the catheters impregnated with the antimicrobial agent by the method of the present invention did not appreciably change by rinsing or even milking in water.

The impregnated catheters were then suspended in human urine for 7 days. The suspending urine was changed at day 3 and all catheters were suspended in urine from the same source. Table 1 summarizes the results of the zones of inhibition (Z.I.) produced by 18-fr silicone, 18-fr polyurethane and 16-fr polyethylene urinary catheters (all of these urinary catheters have a diameter of about 4 mm) at various intervals (D 0: initially prior to suspension in urine; D 1: one day after suspension; D 7: seven days after suspension; ND: not done). A zone of inhibition of 10 mm or greater indicated antimicrobial efficacy.

TABLE 1

| Catheter | Zone of Inhibition (Z.I.) in millimeters (m.m.) | | | |
|---|---|---|---|---|
| | Organism | D 0 | D 1 | D 7 |
| 18-fr silicone | E. coli | 29 | 22 | 12 |
| 18-fr polyurethane | E. coli | 31 | 25 | 18 |
| 16-fr polyethylene | E. coli | ND | 8 | 7 |
| 18-fr silicone | P. aerug. | 22 | ND | 10 |
| 18-fr polyurethane | P. aerug. | 29 | ND | 12 |
| 16-fr polyethylene | P. aerug. | ND | ND | 5 |

The impregnated catheters were also studied by high performance liquid chromatography (HPLC) to determine the levels of antibiotics that are bound to the impregnated urinary catheters at day 0, prior to incubation in urine. Table 2 shows the HPLC determined levels of antibiotics bound to the catheters.

TABLE 2

| Catheter | Minocycline (µg/cm) | Rifampin (µg/cm) |
|---|---|---|
| 18-fr silicone | 584 | 683 |
| 18-fr polyurethane | 2582 | 5140 |

EXAMPLE 2

Comparative Efficacy of 7-fr Polyurethane Vascular Catheters 7-fr polyurethane vascular catheters (2 mm diameter) were coated with the combination of minocycline and rifampin using either the TDMAC method or the method of the present invention. An Arrow Guard vascular catheter coated with a combination of antiseptics (silver sulfadiazine and chlorhexidine) was also compared. Using the impregnation method of the present invention, catheters were dipped for one hour in an antimicrobial solution containing 25 mg of minocycline and 40 mg of rifampin per ml of mixture of organic solvents (methanol plus butyl acetate, 15:85 volume ratio), and 5 mg of NaOH per ml of methanol. Table 3 shows the comparative efficacy of the catheters coated by the Arrow Guard method, the TDMAC method and the impregnation method of the present invention upon initial exposure to cultures of *Staphylococcus epidermidis, Pseudomonas aeruginosa,* and *Candida albicans*.

TABLE 3

| Catheter | Initial Zone of Inhibition Against Organism (m.m.) | | |
|---|---|---|---|
| | *Staph. epi.* | *P. aerug.* | *Candida* |
| Arrow Guard | 15 | 3 | 8 |
| TDMAC | 33 | 9 | 8 |
| Impregnation | 37 | 16 | 17 |

These results demonstrate that the impregnation method of the present invention is more effective against *staphylococcus epidermidis* than either the Arrow Guard or TDMAC methods. Moreover, the impregnation method is effective against *Pseudomonas aeruginosa* and *Candida albicans,* while the TDMAC and Arrow Guard coated catheters are not effective against these organisms (i.e. the zones of inhibition are less than 10 mm).

The coated 7-fr polyurethane vascular catheters were also incubated in serum for sixty days and the efficacy of the coated catheter against *Staphylococcus epidermidis* was measured at certain intervals throughout the period as shown in Table 4 below.

TABLE 4

| | Zones of inhibition against *Staph. epi.* while incubating in serum (mm) | | | | | | | |
|---|---|---|---|---|---|---|---|---|
| Catheter | Day 0 | Day 3 | Day 7 | Day 10 | Day 15 | Day 30 | Day 45 | Day 60 |
| TDMAC | 33 | 28 | 26 | 22 | 11 | 0 | 0 | 0 |
| Impregnation | 37 | 33 | 27 | 26 | 26 | 24 | 20 | 8 |

These results show that the efficacy against *staphylococcus epidermidis* of the impregnated catheter (between 45 and 60 days) is maintained longer than the efficacy of the TDMAC coated catheter (between 15 and 30 days). This is due in part to the greater amount of antimicrobial substance that is imparted to the catheter by impregnation.

The impregnated catheters were also subjected to high performance liquid chromatography (HPLC) to determine the levels of antibiotics that are bound to the impregnated vascular catheters from day 0 through day 45 of incubation in serum. Table 5 shows the HPLC determined levels of antibiotics bound to the catheters at the specified time periods.

TABLE 5

| | Minocycline/Rifampin levels by HPLC before/ after incubation in serum (µg/cm) | | | | | | |
|---|---|---|---|---|---|---|---|
| Catheter | Day 0 | Day 1 | Day 2 | Day 3 | Day 15 | Day 30 | Day 45 |
| TDMAC | 139/ 14 | 123/ 13 | N.D. | 77/ 8 | 21.5/ 3.3 | 9.2/ 0.3 | N.D. |
| Impregnation | 675/ 744 | 321/ 457 | 266/ 433 | 163/ 220 | 51/ 166 | 17/ 83 | 11/ 51 |

N.D.—Not Done.

These results demonstrate that practice of the impregnation method results in higher initial levels of minocycline and rifampin in the coated catheter than by the TDMAC method. The levels of minocycline and rifampin remaining in the catheter are also greater for the impregnated catheter for the time period tested.

EXAMPLE 3

Persistence of Antimicrobial Activity of 7-fr Polyurethane Antibiotic-Impregnated Vascular Catheters after Gas Sterilization The antimicrobial activity of 7-fr polyurethane vascular catheters (2 mm diameter) coated with minocycline and rifampin using the TDMAC method have been previously shown not to be affected by gas sterilization or by gamma irradiation (2–3 Mega rad). Here, 7-fr polyurethane vascular catheters (2 mm diameter) were coated with antibiotics using the impregnation method of the present invention. The catheters were dipped for one hour in an antimicrobial solution containing 25 mg of minocycline and 40 mg of rifampin per ml of mixture of organic solvents (methanol plus butyl acetate, 15:85 volume ratio), and 5 mg of NaOH per ml of methanol. The impregnated catheters were dried, rinsed, milked then dried again, and the efficacy against *Staphylococcus epidermidis, Enterococcus faecalis,* and *Escherichia coli* was measured. The catheters were then subjected to gas sterilization and the efficacy was again measured. Table 6 shows the efficacy of the coated catheter against these organisms before and after gas sterilization. It is noted that the catheters coated by the impregnation method exhibit persistent antimicrobial activity after gas sterilization.

TABLE 6

| | Zone of Inhibition (m.m.) | | | | |
| --- | --- | --- | --- | --- | --- |
| | Staph. epi. | Enterococcus | E. coli | P. aerug. | Candida |
| Before gas sterilization | 37 | 26 | 19 | 16 | 17 |
| After gas sterilization | 33 | 24 | 19 | 13 | 17 |

EXAMPLE 4

Persistence of Antimicrobial Activity of 18-fr Silicone Antibiotic-Impregnated Urinary (Foley) Catheters after Gas Sterilization 18-fr silicone urinary (foley) catheters (4 mm diameter) were coated with antibiotics using the impregnation method of the present invention. The catheters were dipped for one hour in an antimicrobial solution containing 25 mg of minocycline and 40 mg of rifampin per ml of mixture of organic solvents (methanol plus butyl acetate, 15:85 volume ratio), and 5 mg of NaOH per ml of methanol. The catheters were then dried, rinsed, milked then dried again and the efficacy against *Enterococcus faecalis, Escherichia coli, Pseudomonas aeruginosa* and *Candida albicans* were measured. The catheters were then subjected to gas sterilization with ethylene oxide and the efficacy was again measured. Table 7 shows the efficacy of the coated catheter against these organisms before and after gas sterilization. The results show that gas sterilization does not significantly affect the efficacy of the antimicrobial agent as applied by the method of the present invention.

TABLE 7

| | Zone of Inhibition (m.m.) | | | |
| --- | --- | --- | --- | --- |
| | Enterococcus | E. coli | P. aerug. | Candida |
| Before gas sterilization | 29 | 29 | 17 | 19 |
| After gas sterilization | 29 | 28 | 16 | 18 |

EXAMPLE 5

Efficacy of Antibiotic-Impregnated Vascular Grafts

Vascular grafts made of Gortex, Dacron or Gelseal were coated with an antimicrobial agent utilizing the impregnation method of the present invention. The catheters were dipped for one hour in a coating solution containing 25 mg of minocycline and 40 mg of rifampin per ml of mixture of organic solvents (methanol plus butyl acetate, 15:85 volume ratio), and 5 mg of NaOH per ml of methanol. The grafts were then exposed to a culture of *Staphylococcus epidermidis* to determine the efficacy of the antimicrobial impregnated grafts. Table 8 shows that the grafts impregnated with the above mixture of minocycline, rifampin, organic solvent and NaOH exhibits an initial effective antimicrobial effect against *Staphylococcus epidermidis*.

TABLE 8

| Device | Zone of Inhibition (m.m.) Staph. epi. |
| --- | --- |
| Gortex vascular graft (4 mm diameter) | 22 |
| Dacron vascular graft (20 mm diameter) | 33 |
| Gelseal vascular graft (8 mm diameter) | 26 |

Gortex: polytetrafluoroethylene
Dacron: polyethylene tetraphthalate
Gelseal: Dacron sealed with gelatin

EXAMPLE 6

Efficacy of Antibiotic-Impregnated Urinary Catheters

A combination of antimicrobial agents applied to 16-fr polyethylene urinary catheters (bladder catheters that are inserted suprapubically) utilizing the impregnation method of the present invention. The catheters were dipped for one hour in a coating solution containing 15 mg of minocycline and 30 mg of rifampin per ml of mixture of organic solvents (methanol plus butyl acetate, 15:85 volume ratio), and 10 mg of NaOH per ml of methanol.

A combination of antimicrobial agents was also applied to 18-fr polyurethane urinary catheters (nephrostomy catheters that are inserted into the kidney) utilizing the impregnation method of the present invention. The catheters were dipped for one hour in a coating solution containing 25 mg of minocycline and 40 mg of rifampin per ml of mixture of organic solvents (methanol plus butyl acetate, 15:85 volume ratio), and 5 mg of NaOH per ml of methanol. The data shown below in Table 9 indicates that the antimicrobial impregnated 16-fr polyethylene urinary catheter is effective against *Escherichia coli*, but not *Pseudomonas aeruginosa* or *Candida albicans*. The results also show that the antimicrobial impregnated 18-fr polyurethane urinary catheter is effective against *Escherichia coli, Pseudomonas aeruginosa* and *Candida albicans* (zones of inhibition greater than 10 mm). This indicates that polyurethane is generally more receptive to impregnation than polyethylene.

TABLE 9

| Device | Zone of Inhibition (m.m.) | | |
| --- | --- | --- | --- |
| | E. coli | P. aerug. | Candida |
| 16 fr polyethylene urinary catheters | 20 | 8 | 8 |
| 18 fr polyurethane urinary catheters | 29 | 24 | 27 |

EXAMPLE 7

Effect of Varying Concentrations of NaOH and Antibiotics in Impregnation Solution on Antimicrobial Efficacy of 7-fr Polyurethane Vascular Catheters The concentrations of NaOH and antibiotics in the antimicrobial solution were varied, and the various coatings were applied to 7-fr polyurethane vascular catheters. The first catheter was not exposed to the coating process. The second catheter was impregnated with a solution of butyl acetate, methanol and NaOH, but no antimicrobial agent. The third catheter was impregnated with a solution of butyl acetate and methanol without NaOH or an antimicrobial agent. The fourth catheter was dipped in an antimicrobial solution containing 15 mg of minocycline and 30 mg of rifampin per ml of mixture of organic solvents (methanol plus butyl acetate, 15:85 volume ratio), without NaOH. The fifth catheter was dipped in an antimicrobial solution containing 15 mg of minocycline and 30 mg of rifampin per ml of mixture of organic solvents (methanol plus butyl acetate, 15:85 volume ratio), and 10 mg of NaOH per ml of methanol. The sixth catheter was dipped in an antimicrobial solution containing 25 mg of minocycline and 40 mg of rifampin per ml of mixture of organic solvents (methanol plus butyl acetate, 15:85 volume ratio), and 5 mg of NaOH per ml of methanol. The seventh catheter was dipped in an antimicrobial solution containing 40 mg of minocycline and 80 mg of rifampin per ml of mixture of organic solvents (methanol plus butyl acetate, 15:85 volume ratio), and 5 mg of NaOH per ml of methanol. Table 10 shows the antimicrobial efficacy of each of the various solution coated catheters against *Staphylococcus epidermidis, Pseudomonas aeruginosa,* and *Candida albicans.* Table 10 also shows the levels of minocycline and rifampin bound to the material of the impregnated catheter.

TABLE 10

| [Mino/ Rif] µg/ml | NaOH mg/ml | Zone of Inhibition (m.m.) | | | [Mino/Rif] µg/cm of cath |
|---|---|---|---|---|---|
| | | Staph. epi. | P. aerug. | Candida | |
| 0/0 | 0 | 0 (catheter not processed) | | | |
| 0/0 | 5 | 0 (catheter processed with butyl acetate/ methanol and NaOH) | | | |
| 0/0 | 0 | 0 (catheter processed with butyl acetate/ methanol but without NaOH) | | | |
| 15/30 | 0 | 27 | 10 | 12 | 35/25 |
| 15/30 | 10 | 33 | 14 | 13 | N.D. |
| 25/40 | 5 | 37 | 16 | 17 | 675/744 |
| 40/80 | 5 | 37 | 20 | 18 | 1377/1817 |

N.D.—Not Done.

These findings indicate that the addition of NaOH and raising the concentration of antibiotics in the coating solution increase the antimicrobial efficacy of coated catheters.

EXAMPLE 8

Effect of Varying Concentrations of NaOH and Antibiotics in Impregnation Solution on Antimicrobial Efficacy of 18-fr Silicone Urinary (Foley) Catheters The concentrations of NaOH and antibiotics in the antimicrobial solution were varied, and the various coating were applied to 18-fr silicone urinary (Foley) catheters. The first catheter was dipped in an antimicrobial solution containing 15 mg of minocycline and 30 mg of rifampin per ml of mixture of organic solvents (methanol plus butyl acetate, 15:85 volume ratio), and 10 mg of NaOH per ml of methanol. The second catheter was dipped in an antimicrobial solution containing 25 mg of minocycline and 40 mg of rifampin per ml of mixture of organic solvents (methanol plus butyl acetate, 15:85 volume ratio), and 5 mg of NaOH per ml of methanol. The third catheter was dipped in an antimicrobial solution containing 40 mg of minocycline and 80 mg of rifampin per ml of mixture of organic solvents (methanol plus butyl acetate, 15:85 volume ratio), and 5 mg of NaOH per ml of methanol. Table 11 shows the antimicrobial efficacy of each of the various solution coated catheters against, *Pseudomonas aeruginosa, Escherichia coli* and *Candida albicans.* Table 11 also shows the levels of minocycline and rifampin present in the material of the impregnated catheter.

TABLE 11

| [Mino/Rif] µg/ml | NaOH mg/ml | Zones of Inhibition (m.m.) | | | [Mino/Rif] µg/cm of cath |
|---|---|---|---|---|---|
| | | P. aerug. | E. coli | Candida | |
| 15/30 | 10 | 17 | 21 | 17 | 718/N.D. |
| 25/40 | 5 | 24 | 29 | 19 | 3263/4177 |
| 40/80 | 5 | 24 | 36 | 24 | N.D. |

N.D.—Not Done.

These findings indicate that increasing the concentration of antibiotics in the coating solution generally leads to greater antimicrobial efficacy of coated catheters.

EXAMPLE 9

Effect of Varying Time of Dipping 7-fr Polyurethane Vascular Catheters in Impregnation Solution on Antimicrobial Efficacy 7-fr vascular polyurethane catheters were dipped in two different antimicrobial solutions for different time periods. The first group of catheters were dipped in a solution containing 10 mg of minocycline and 30 mg of rifampin per ml of mixture of organic solvents (methanol plus butyl acetate, 15:85 volume ratio), and no NaOH. The second group of catheters were dipped in an antimicrobial solution containing 25 mg of minocycline and 40 mg of rifampin per ml of mixture of organic solvents (methanol plus butyl acetate, 15:85 volume ratio), and 5 mg of NaOH per ml of methanol. Catheters from each group were dipped in the solution for periods of 15, 30, 60 and 120 minutes to determine the optimum time period necessary to provide an effective antimicrobial coating, as shown in Table 12 below.

TABLE 12

| [Mino/ Rif] µg/ml | NaOH mg/ml | Dipping Time (minutes) | Zone of Inhibition (m.m.) | | | [Mino/ Rif] µg/ cm of cath |
|---|---|---|---|---|---|---|
| | | | Staph. epi. | P. aerug. | Candida | |
| 10/30 | 0 | 15 | 32 | 12 | 12 | 132/270 |
| 10/30 | 0 | 30 | 36 | 18 | 13 | 320/701 |
| 10/30 | 0 | 60 | 34 | 15 | 12 | 356/878 |
| 10/30 | 0 | 120 | 33 | 16 | 13 | 361/890 |
| 25/40 | 5 | 15 | 35 | 16 | 14 | 286/294 |
| 25/40 | 5 | 30 | 34 | N.D. | 15 | 520/537 |
| 25/40 | 5 | 60 | 33 | 16 | 15 | 739/841 |
| 25/40 | 5 | 120 | 33 | 15 | 16 | N.D. |

N.D.—Not Done.

These results demonstrate that longer periods of dipping of catheters are associated with higher levels of antibiotics on coated catheters (60 min>30 min>15 min). However, there are no notable differences in the efficacy of antimicrobial coated catheters that were coated for 120 minutes versus 60 minutes.

EXAMPLE 10

Efficacy of 7-fr Polyurethane Vascular Catheters Impregnated with an Antimicrobial Solution including Nafcillin or Erythromycin 7-fr polyurethane vascular catheters were coated with nafcillin at a concentration of 10 mg/ml of a mixture of organic solvents (butylacetate:methanol=50:50) without NaOH. 7-fr polyurethane vascular catheters were also coated with erythromycin at a concentration of 10 mg/ml of a mixture of organic solvents (butylacetate:methanol=50:50) without NaOH. The zones of inhibition against *Staphylococcus aureus* are shown below in Table 13, and demonstrate the efficacy of the catheters impregnated with nafcillin and erythromycin (i.e. Z.I.>10 mm).

TABLE 13

| Antibiotic | Zone of Inhibition (m.m.) Staph. aur. |
| --- | --- |
| Nafcillin | 25 |
| Erythromycin | 17 |

EXAMPLE 11

Efficacy of Various Polymeric Antibiotic-Impregnated Urinary Catheters

Urinary (Bladder) catheters were dipped for one hour in a coating solution containing 25 mg of minocycline and 40 mg of rifampin per ml of mixture of organic solvents (methanol plus butyl acetate, 15:85 volume ratio), and 5 mg of NaOH per ml of methanol. The results were as follows:

| Catheter | Zone of Inhibition against Enterococcus (m.m.) |
| --- | --- |
| Red rubber (12-fr) | 28 |
| Rubber latex coated with teflon (16-fr) | 27 |
| Latex coated with silicone (18-fr) | 30 |
| Plastic (12-fr) | 25 |

The results demonstrate that catheters comprised of the above materials and impregnated with the specified antimicrobial coating are effective against the *Enterococcus faecalis* bacteria (i.e. Z.I.>10 mm).

EXAMPLE 12

Efficacy of 7-fr Polyurethane Vascular Catheters Impregnated with an Antimicrobial Solution including Hexachlorophene 7-fr polyurethane vascular catheters were coated with hexachlorophene at a concentration of 10 mg/ml of mixture of organic solvents (methanol plus butyl acetate, 15:85 volume ratio) without NaOH. The zones of inhibition against *Staphylococcus epidermidis* and *Enterococcus faecalis* were 11 and 12 mm, respectively. The results demonstrate that antiseptics, as well as antibiotics, and combinations thereof can be effectively used as an antimicrobial agent in impregnating the material of non-metallic medical devices such as catheters.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

The present invention, therefore, is well adapted to carry out the objects and attain the ends and advantages mentioned as well as others inherent therein. While presently preferred embodiments of the invention are given for the purpose of disclosure, numerous changes in the details will readily suggest themselves to those skilled in the art and which are encompassed within the spirit of the invention and the scope of the appended claims.

What we claim is:

1. A method for impregnating a non-metallic medical implant with an antimicrobial agent comprising the steps of:

forming an antimicrobial composition of an effective concentration to inhibit the growth of bacterial and fungal organisms relative to uncoated implants by dissolving the antimicrobial agent in an organic solvent;

adding a separate penetrating agent to the composition;

adding an alkalinizing agent to the composition; and applying the antimicrobial composition to at least a portion of the medical implant under conditions where the antimicrobial composition permeates the material of the medical implant.

2. The method for impregnating a non-metallic medical implant according to claim 1, wherein the medical implant is made from rubber or plastic.

3. The method for impregnating a non-metallic medical implant according to claim 1, wherein the alkalinizing agent is selected from the group consisting of sodium hydroxide, potassium hydroxide, ammonia in water, diethylamine, and triethylamine.

4. The method for impregnating a non-metallic medical implant according to claim 1, wherein the alkalinizing agent comprises sodium hydroxide.

5. The method for impregnating a non-metallic medical implant according to claim 1, further comprising the step of heating the solution.

6. The method for impregnating a non-metallic medical implant according to claim 5, wherein the solution is heated to a temperature between about 30° C. and 70° C.

7. The method for impregnating a non-metallic medical implant according to claim 1, wherein the step of applying the antimicrobial composition to the medical implant comprises dipping the implant in the composition for a period of between 15 and 120 minutes, and removing the impregnated medical implant from the antimicrobial composition.

8. The method for impregnating a non-metallic medical implant according to claim 7, wherein the medical implant is dipped in the solution for a period of approximately 60 minutes.

9. The method for impregnating a non-metallic medical implant according to claim 1, further comprising the steps of rinsing with a liquid and milking the impregnated medical implant.

10. The method for impregnating a non-metallic medical implant according to claim 1, wherein the bacterial and fungal organisms are selected from the group consisting of gram-positive bacteria, gram-negative bacilli and Candida.

11. The method for impregnating a non-metallic medical implant according to claim 1, wherein the organic solvent is selected from the group consisting of alcohols, ketones, ethers, aldehydes, acetonitrile, acetic acid, methylene chloride and chloroform.

12. The method for impregnating a non-metallic medical implant according to claim 11, wherein the organic solvent is methanol.

13. The method for impregnating a non-metallic medical implant according to claim 1, wherein the penetrating agent is selected from the group consisting of esters, ketones, methylene chloride and chloroform.

14. The method for impregnating a non-metallic medical implant according to claim 13, wherein the penetrating agent is an ester selected from the group consisting of butyl acetate, ethyl acetate, propyl acetate, amyl acetate and combinations thereof.

15. The method for impregnating a non-metallic medical implant according to claim 1, wherein the step of forming an antimicrobial composition further comprises adding a salt exhibiting a high ionic strength.

16. The method for impregnating a non-metallic medical implant according to claim 1, wherein the medical implant is made from a material selected from the group consisting of silicone, polyurethane, polyethylene, polytetrafluoroethylene, polyethylene tetraphthalate and polyethylene tetraphthalate sealed with gelatin, collagen or albumin.

17. The method for impregnating a non-metallic medical implant according to claim 1, wherein the medical implant is a vascular catheter selected from the group consisting of peripherally insertable central venous catheters, dialysis catheters, tunneled central venous catheters, peripheral venous catheters, central venous catheters, arterial catheters and pulmonary artery Swan-Ganz catheters.

18. The method for impregnating a non-metallic medical implant according to claim 1, wherein the medical implant is a urinary catheter.

19. The method for impregnating a non-metallic medical implant according to claim 1, wherein the medical implant is a vascular graft.

20. The method for impregnating a non-metallic medical implant according to claim 1, wherein the medical implant is selected from the group consisting of vascular catheter ports, wound drain tubes, hydrocephalus shunts, peritoneal dialysis catheters, pacemaker capsules, artificial urinary sphincters, joint replacements, urinary dilators, urinary devices, tissue bonding urinary devices, penile prostheses and heart valves.

21. The method for impregnating a non-metallic medical implant according to claim 1, wherein the antimicrobial agent is selected from the group consisting of antibiotics, antiseptics and disinfectants.

22. The method for impregnating a non-metallic medical implant according to claim 21, wherein the antimicrobial agent is an antibiotic selected from the group consisting of tetracyclines, penicillins, macrolides, rifampin and combinations thereof.

23. The method for impregnating a non-metallic medical implant according to claim 21, wherein the antimicrobial agent is an antibiotic comprising a combination of minocycline and rifampin.

24. The method for impregnating a non-metallic medical implant according to claim 21, wherein the antimicrobial agent is an antiseptic comprising hexachlorophene.

25. A method for impregnating a non-metallic medical device formed of a polymeric material with an antimicrobial agent comprising the steps of:

forming an antimicrobial solution of an effective concentration to inhibit the growth of bacterial and fungal organisms relative to uncoated non-metallic medical device implants by dissolving an alkalinizing agent selected from the group consisting of sodium hydroxide and potassium hydroxide in methanol, dissolving minocycline and rifampin in the solution, adding a penetrating agent selected from the group consisting of butyl acetate, ethyl acetate and combinations thereof to the solution;

heating the antimicrobial solution to a temperature of between 30° C. and 70° C.;

dipping at least a portion of the non-metallic medical device in said antimicrobial solution under conditions where the antimicrobial solution permeates the polymeric material of the non-metallic medical device; and removing the non-metallic medical device from the solution.

26. The method for impregnating a non-metallic medical device according to claim 25, wherein the polymeric material is selected from the group consisting of silicone, polyurethane, polyethylene, polytetrafluoroethylene, polyethylene tetraphthalate and polyethylene tetraphthalate sealed with gelatin, collagen or albumin.

27. The method for impregnating a non-metallic medical device according to claim 25, wherein the bacterial and fungal organisms are selected from the group consisting of gram-positive bacteria, gram-negative bacilli and Candida.

28. A method for impregnating a non-metallic medical device formed of a polymeric material with an antimicrobial agent comprising the steps of:

forming an antimicrobial solution of an effective concentration to inhibit the growth of bacterial and fungal organisms relative to uncoated non-metallic medical device implants by dissolving an alkalizing agent selected from the group consisting of sodium hydroxide and potassium hydroxide in methanol, dissolving minocycline and rifampin in the solution, adding methylene chloride to the solution;

heating the antimicrobial solution to a temperature of between 30° C. and 70° C.;

dipping at least a portion of the non-metallic medical device in said antimicrobial solution under conditions where the antimicrobial solution permeates the polymeric material of the non-metallic medical device; and removing the non-metallic medical device from the solution.

29. The method for impregnating a non-metallic medical device according to claim 28, wherein the polymeric material is selected from the group consisting of silicone, polyurethane, polyethylene, polytetrafluoroethylene, polyethylene tetraphthalate and polyethylene tetraphthalate sealed with gelatin, collagen or albumin.

30. The method for impregnating a non-metallic medical device according to claim 28, wherein the bacterial and fungal organisms are selected from the group consisting of gram-positive bacteria, gram-negative bacilli and Candida.

31. The method for impregnating a non-metallic medical device according to claim 25, wherein the medical implant is made from rubber or plastic.

32. The method for impregnating a non-metallic medical device according to claim 28, wherein the medical implant is made from rubber or plastic.

33. The method of any of claims 25–30, 31 or 32 wherein the non-metallic medical device is a catheter.

* * * * *